United States Patent [19]
Krenkel et al.

[11] Patent Number: 5,112,340
[45] Date of Patent: May 12, 1992

[54] FIXATION DEVICE WITH FRAME MEMBERS AND PINS

[76] Inventors: Christian Krenkel, Moosstrasse 126, A-5020 Salzburg; Georg Lixl, Untereching 72, A-5110 Oberndorf, both of Austria

[21] Appl. No.: 609,697

[22] Filed: Nov. 5, 1990

[30] Foreign Application Priority Data

Nov. 10, 1989 [DE] Fed. Rep. of Germany ....... 3937555

[51] Int. Cl.⁵ .............................................. A61F 11/00
[52] U.S. Cl. ....................................... 606/130; 606/54
[58] Field of Search .................. 128/845, 857, 20; 606/130, 54, 59

[56] References Cited

U.S. PATENT DOCUMENTS

| | | | |
|---|---|---|---|
| 1,707,689 | 4/1929 | Sloan | 128/20 |
| 3,053,256 | 9/1962 | Cooper et al. | 606/130 |
| 3,223,087 | 12/1965 | Vladyka et al. | 606/130 |
| 4,230,117 | 10/1980 | Anichkov | 606/130 |
| 4,386,602 | 6/1983 | Sheldon et al. | 606/130 |
| 4,465,069 | 8/1984 | Barbier et al. | 606/130 |
| 4,706,665 | 11/1987 | Gouda | 606/130 |

Primary Examiner—Max Hindenburg
Attorney, Agent, or Firm—Wenderoth, Lind & Ponack

[57] ABSTRACT

A device for fixing a point relative to the human body with a pointer is adjustable in three directions. The end indicates the position of the point to be fixed. A frame with three feet can be mounted on pins anchored in the facial part of the skull.

16 Claims, 3 Drawing Sheets

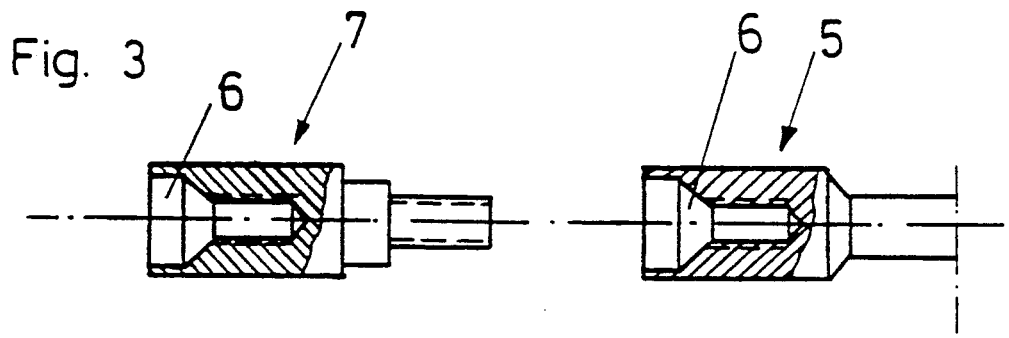
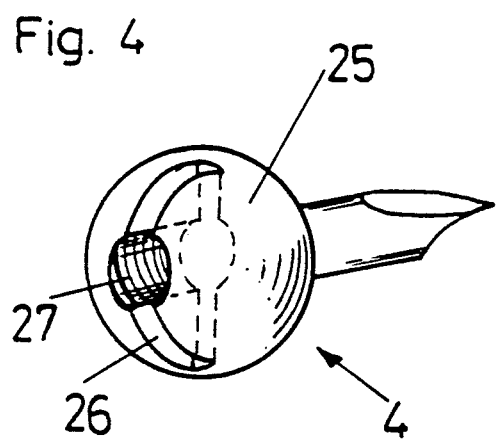
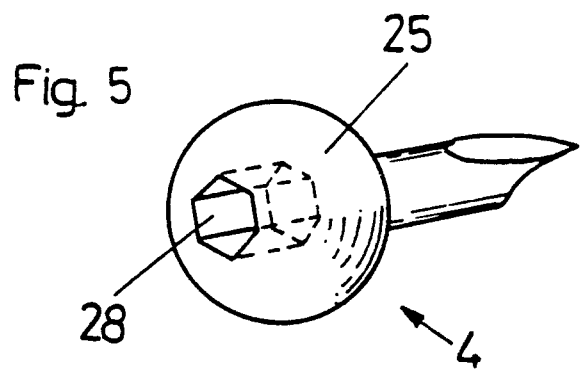

FIXATION DEVICE WITH FRAME MEMBERS AND PINS

BACKGROUND OF THE INVENTION

The object of the invention relates to a device to fix a point relative to the human body, with a frame to be attached to the body and a pointer that is adjustable relative to the frame and 3 whose end indicates the position of the point to be fixed.

In particular during surgical corrections in the maxillofacial region, it is necessary to determine the initial position of a point of the body surface relative to a part of the body that remains unchanged, to set target inputs in order to displace this point, and to check these inputs during the operation. For example, the intended operation can consist of rotating or displacing the upper jaw or perhaps in lifting an eyeball that lies too low by inserting a filler into the orbita. However, the device described below is not restricted to the preferred type of application; it could also be used for the repeated search of points in the brain, for construction of the forehead or the like.

SUMMARY OF THE INVENTION

An important requirement of the device to be provided is that it shall impede as little as possible the surgeon in his work. This requirement is fulfilled by the invention in that a frame with three feet can be mounted on pins anchored in the skeleton, in particular in the facial part of the skull.

Since for the duration of the operation only three pins remain in the skeleton, the surgeon can work without being impeded by the device, but, on the other hand, can bring the device at any time into the initial position again with certainty. The pins, which serve to fix the frame, are preferably designed as Kirschner's wires with ball ends. The ball end makes it possible to mount the hollow ends of the feet of the frame in different directions; with a Kirschner's wire, the design allows the pins to be screwed into the bones due to the boring end that is typical for such wires. The rotating tool required to this end can grasp either a cross slot or, even better, an hexagonal slot of the ball end of the pin. The hexagonal slot has the advantage that it simultaneously guarantees the axial guiding of the pin, for which an additional axial guide bore is provided in another case.

To be able to align the frame of the invention parallel to the frontal plane of the face, it is advantageous if extension pieces can be screwed into the ends of the feet of the frame.

To be able to fix the pins, anchored in the skeleton, in different relative positions depending on the individual anatomical pecularities, preferably it is provided that at least two feet are attached to telescopic arms so that their distance is variable.

Other advantageous embodiments of the invention follow from the dependent claims explained with reference to the drawings.

BRIEF DESCRIPTION OF THE FIGURES

FIG. 3 is a partial sectional view of an end of a foot of the frame of 1 and a matching extension piece;

FIGS. 4 and 5 are schematic views of two designs of pins serving to fix the frame according to FIGS. 1 and 2.

DETAILED DESCRIPTION OF THE PREFERRED EMBODIMENTS

Figure 1:
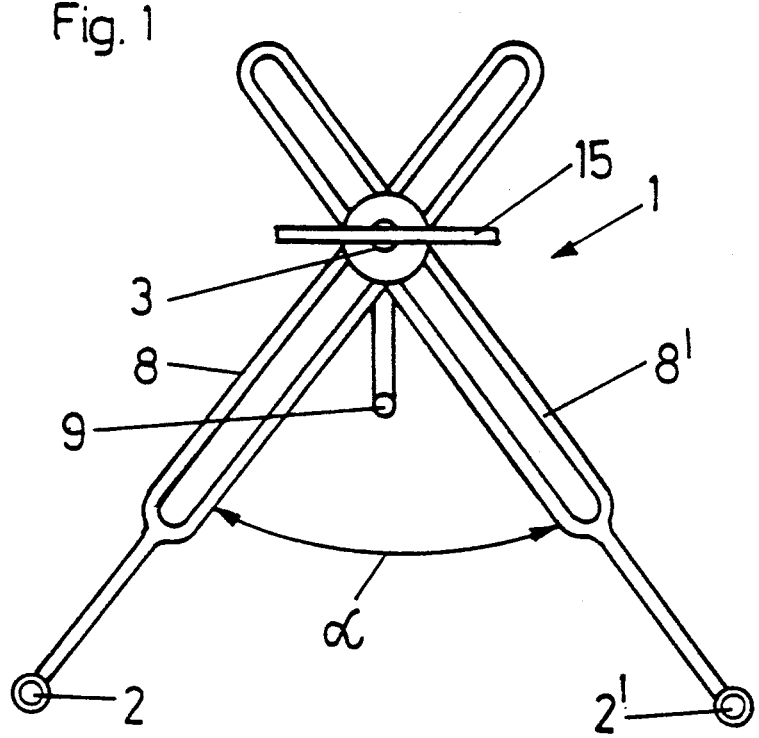
FIGS. 1 and 2 are top and side views, respectively, of an embodiment of the frame.
Figure 2:
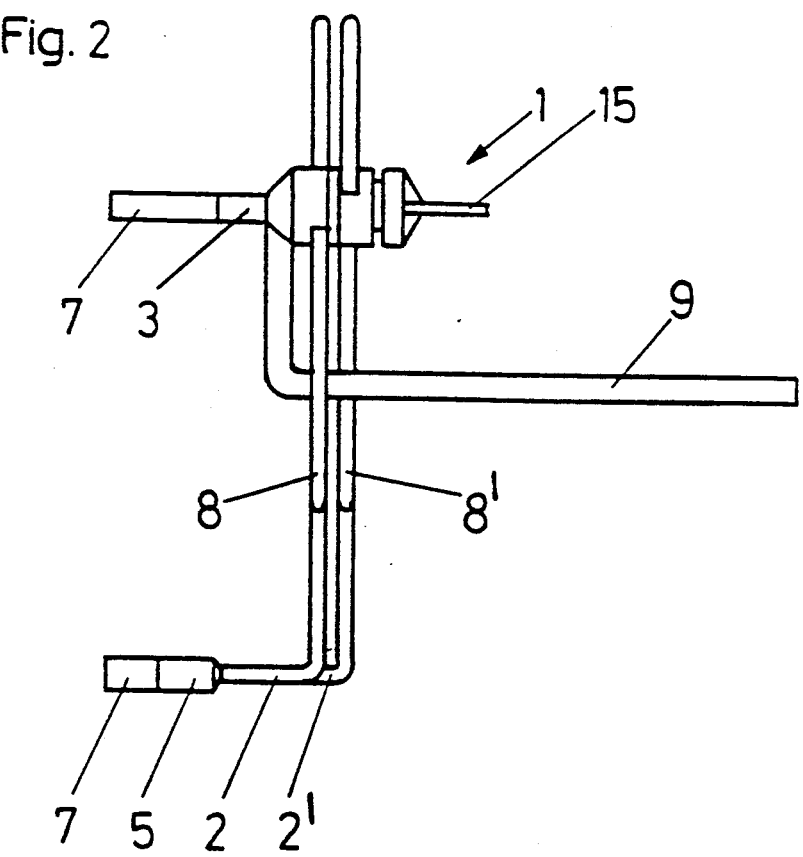

Frame 1, shown in FIG. 1, comprises three feet, 2,2', and 3, whose ends 5 can be mounted directly or by means of extension pieces 7 on pins 4, which can be anchored in the human skeleton. Foot 2 is attached to an arm 8 comprising two rods; foot 2' is attached analogously to arm 8'. Arms 8 and 8' can be adjusted in the longitudinal direction relative to foot 3, where the angle $\alpha$ enclosed by them is variable. The relative position of feet 2,2', and 3 can be fixed by tightening a wing nut 15.

As stated above, frame 1 can be tilted relative to a base by providing it with extension pieces 7 of suitable length in one or two of its feet 2,2' and 3. To this end, ends 5 of the feet are provided with recesses 6 in which extension pieces 7 can be screwed. Owing to the design of the extension pieces 7 shown in FIG. 3, they can be arranged, moreover, in succession.

The pins shown schematically in FIGS. 4 and 5 are enlarged to twice their size as compared with FIG. 3. They are Kirschner's wires with a boring tip, whose ball end 25 fits accurately into recess 6 of ends 5 of feet 2,2' and 3, or extension pieces 7. These pins 4 are rotated in by means of a rotating tool, which in the embodiment of FIG. 4 engages with a cross slot 26 and in the embodiment of FIG. 5 fits into an hexagonal slot 28. With the design of FIG. 5 and FIG. 4, a guide bore 27 is superfluous.

Figure 6:
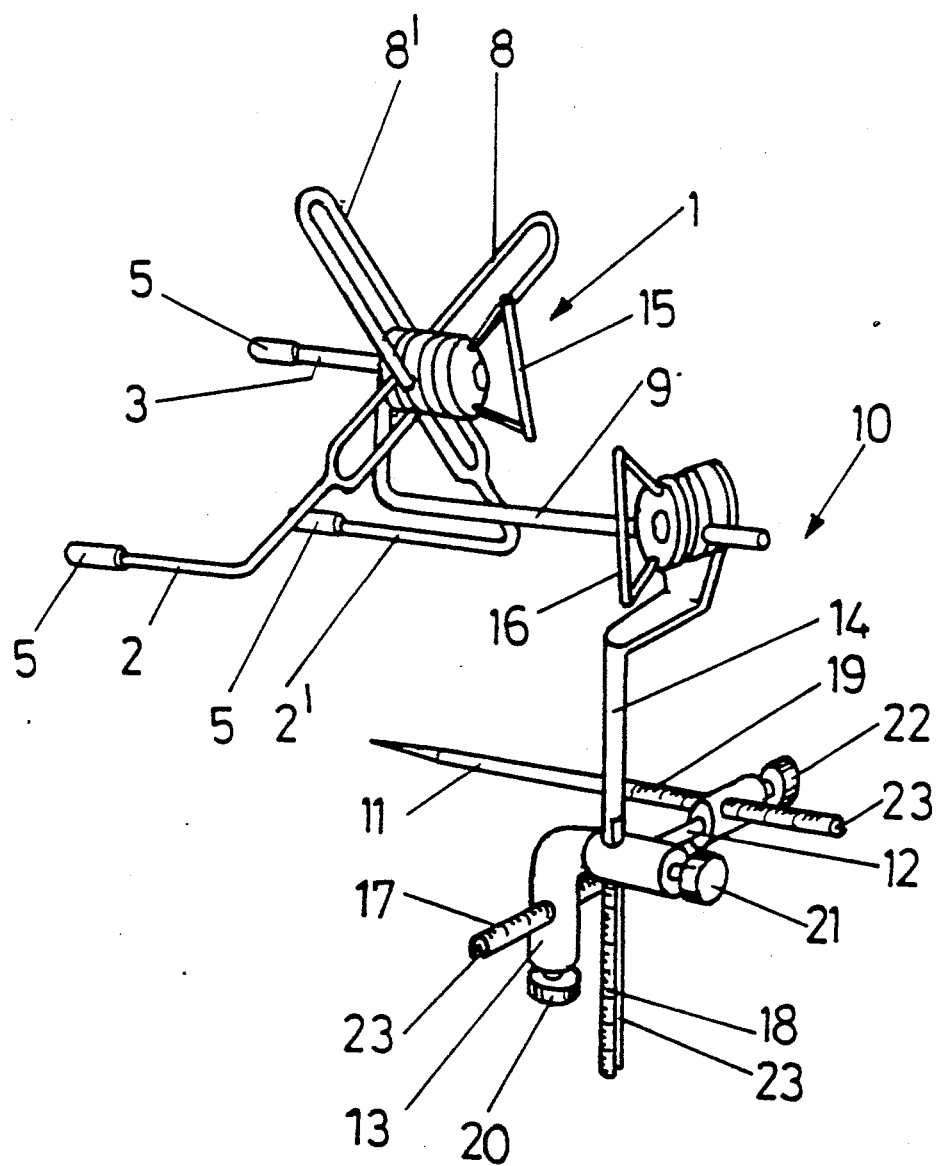
FIG. 6 is a schematic view of the entire device.

As apparent from FIG. 6, frame 1 and a linkage 10 allow the end of an pointer 11 to be moved into any desired position relative to the stationary ends 5 of the feet of frame 1 or the pins 4. To this end, frame 1 comprises a supporting arm 9, which extends normally relative to the plane of the frame which is clamped by means of arms 8 and 8'. At supporting arm 9, a linkage 10, which comprises rods 12 and 14 normally standing one on top of the other and on the pointer 11, can be fixed into different angular positions by means of a wing nut 16. Rod 12 can be displaced in the longitudinal direction on rod 14, where the degree of displacement is visible by means of a scale 18. Twisting of rod 12 around rod 14 is ruled out by a groove 23 with which a setscrew 21 engages, forming a part of a mounting 13 for rod 12. Rod 12 can be displaced in mounting 13 in the longitudinal direction relative to a scale 17 and can be fixed in position by a screw 20. The longitudinal displacement of pointer 11 can be read on scale 19. A screw 22 allows pointer 11 to be fixed in position relative to rod 12.

If the device shown is used for a surgical correction in the maxillofacial region, it is expedient to use a cranial pin, which is placed in the region of the glabella, thus precisely between the eye brows. Beforehand a skull radiograph is checked to see whether the frontal sinus is normal; namely whether drilling the wire into the frontal cavity is harmless. Of course, one should avoid drilling as far as the meninges, which is possible if there is no frontal cavity. The lateral pins are placed symmetrically into the right and left cheek bones, sufficiently spaced from the nervus infraorbitalis, on the one hand, and the nervus zygomaticus, on the other hand. If frame 1 still does not stand parallel to the frontal plane (which in turn normally extends relative to the sagittal plane and Frankfort horizontal plane), this parallel position can be achieved with suitable extension pieces 7. The parallel position is not in itself a prerequisite for the device to function, but aligning the device in accordance with the head planes facilitates determining the displacements resulting during the operation. In addition, maxillofacial operations are performed only after their effect has been simulated in articulators, where with such devices the displacements resulting during the operation are split up according to the planes of the head. Aligning the measuring device according to the planes facilitates the transfer of experience gained with the model operating device to the actual operating process.

If the device presented is used to measure an eyeball, the cranial pin is attached in turn in the glabella region, but a lateral pin at the lateral edge of the nasal cavity facing the eye to be measured and the third pin in the cheek bone further away from the eye to be measured. As stated above, the invention is, however, not restricted to the arrangement of pins 4 at the described points of the human skeleton.

We claim:

1. A device for fixing a point relative to the human body, comprising:
   a frame for attachment to the human body, including a plurality of frame members, each said frame member having a foot portion, and each said foot portion having a connection means for connecting to a pin;
   a pointer adjustably mounted to said frame, said pointer having an indicator end for indicating a point on the human body; and
   a plurality of pins, each said pin comprising a means for anchoring said pin in the human skeleton and a means for detachably connecting said pin to a said connection means of a respective said foot portion.

2. The device of claim 1, wherein said connection means of each said foot portion comprises an end of said foot portion having a concave tapered recess.

3. The device of claim 2, wherein said connection means of each said foot portion further comprises an extension piece threadedly engageable with said end of said foot portion.

4. The device of claim 1, wherein at least two of said members of said frame are telescopic arms telescopically moveable so as to enable the variation of the location of their respective said foot portions.

5. The device of claim 4, wherein said telescopic arms of said frame form an angle therebetween, and said telescopic arms are further moveable to enable the variation of said angle.

6. The device of claim 1, wherein said frame further comprises a supporting arm extending in a direction opposite to said foot portions and a linkage attachable to said supporting arm bearing said pointer.

7. The device of claim 6, wherein said supporting arm is pivotably mounted to said frame members so as to be pivotable about a said foot portion.

8. The device of claim 6, wherein said linkage comprises a first rod adjustably mounted to said supporting arm, a mounting slidably mounted on said first rod, and a second rod slidably mounted in said mounting in a direction transverse to said first rod, wherein said pointer is slidably mounted to said second rod, extending slidably in a direction perpendicular to said second rod and said first rod.

9. The device of claim 1, wherein said means for anchoring of each said pin comprises a Kirschner's wire, and said means for detachably connecting each said pin to a said connection means comprises a ball on the end of said pin.

10. The device of claim 9, wherein each said ball of said pins has a cross slot for engagement with a rotating tool.

11. The device of claim 10, wherein each said pin has an axial guide bore therein extending in said ball of said pin.

12. The device of claim 9, wherein each said ball of said pins has a hexagonal slot therein for engagement with a rotating tool.

13. A pin for connection to the human skeleton for a frame to be attached to the human body, said pin comprising:
   a means for anchoring the pin in the human skeleton, said means comprising a Kirschner's wire; and
   a means for detachably connecting the pin to a corresponding connection on the frame, said means comprising ball forming an end of the pin.

14. The pin of claim 13, wherein said ball has a cross slot for engagement with a rotating tool.

15. The pin of claim 14, wherein said ball has an axial guide bore extending therein.

16. The pin of claim 13, wherein said ball has a hexagonal slot therein for engagement with a rotating tool.

* * * * *